US00PP23498P2

(12) United States Plant Patent
Podaras

(10) Patent No.: US PP23,498 P2
(45) Date of Patent: Mar. 26, 2013

(54) ***BUDDLEIA* PLANT NAMED 'HINEBUD1'**

(50) Latin Name: ***Buddleia* hybrid**
Varietal Denomination: Hinebud1

(75) Inventor: Peter C. Podaras, Davis, CA (US)

(73) Assignee: Hines Growers LLC, Laguna Hills, CA (US)

( * ) Notice: Subject to any disclaimer, the term of this patent is extended or adjusted under 35 U.S.C. 154(b) by 0 days.

(21) Appl. No.: 13/199,738

(22) Filed: Sep. 7, 2011

(51) Int. Cl.
*A01H 5/00* (2006.01)

(52) U.S. Cl. ..... Plt./242

(58) Field of Classification Search ..... Plt./242
See application file for complete search history.

(56) References Cited

U.S. PATENT DOCUMENTS

PP22,098 P2 * 8/2011 Podaras ..... Plt./242

* cited by examiner

*Primary Examiner* — Howard Locker
(74) *Attorney, Agent, or Firm* — Barbara Campbell; Cochran Freund & Young LLC

(57) ABSTRACT

A *Buddleia* plant particularly distinguished by a low-growing and spreading growth habit, large, pendulous inflorescence and suitable for use in hanging baskets, containers, and beddings, is disclosed.

1 Drawing Sheet

Genus and species: *Buddleia* hybrid.
Variety denomination: 'Hinebud1'.

BACKGROUND OF THE NEW PLANT

The present invention comprises a new and distinct variety of *Buddleia*, botanically known as *Buddleia* hybrid, and hereinafter referred to by the variety name 'Hinebud1'. The new variety originated from a cross-pollination conducted in Winters, Calif. in July 2010 between the female *Buddleia* parent, an un-named seedling (unpatented) and the male *Buddleia* parent, 'Podaras #12' U.S. Plant Pat. No. 22,098). The female parent is a complex hybrid of *Buddleia davidii*×*Buddleia alternifolia*×*Buddleia caryopterifolia*×*Buddleia lindleyana*×*Buddleia crispa*. The male parent is a hybrid of *Buddleia davidii*×*Buddleia alternifolia)*×*Buddleia davidii*. A single plant selection was subsequently chosen for further evaluation and asexual propagation.

The new plant was first asexually propagated on Sep. 15, 2010 in Winters, Calif. and has been asexually reproduced by cuttings for three generations in Winters, Calif. The present invention has been found to retain its distinctive characteristics through successive asexual propagations by softwood cuttings.

'Hinebud1' has not been made publicly available or sold more than one year prior to the filing of this application.

SUMMARY OF THE INVENTION

The following are the most outstanding and distinguishing characteristics of the new variety when grown under normal horticultural practices in Winters, Calif.

1. A low-growing and spreading growth habit;
2. Large, pendulous inflorescence; and
3. For use in hanging baskets, containers and beddings.

DESCRIPTION OF THE PHOTOGRAPHS

This new *Buddleia* plant is illustrated by the accompanying photographs which show the overall plant habit, foliage and inflorescence of the plant. The colors are as true as can be reasonably obtained by conventional photographic procedures. The photographs are of a one-year old plant grown in a greenhouse and outdoors in Winters, Calif. in August 2011.

DESCRIPTION OF THE NEW VARIETY

Figure 1:
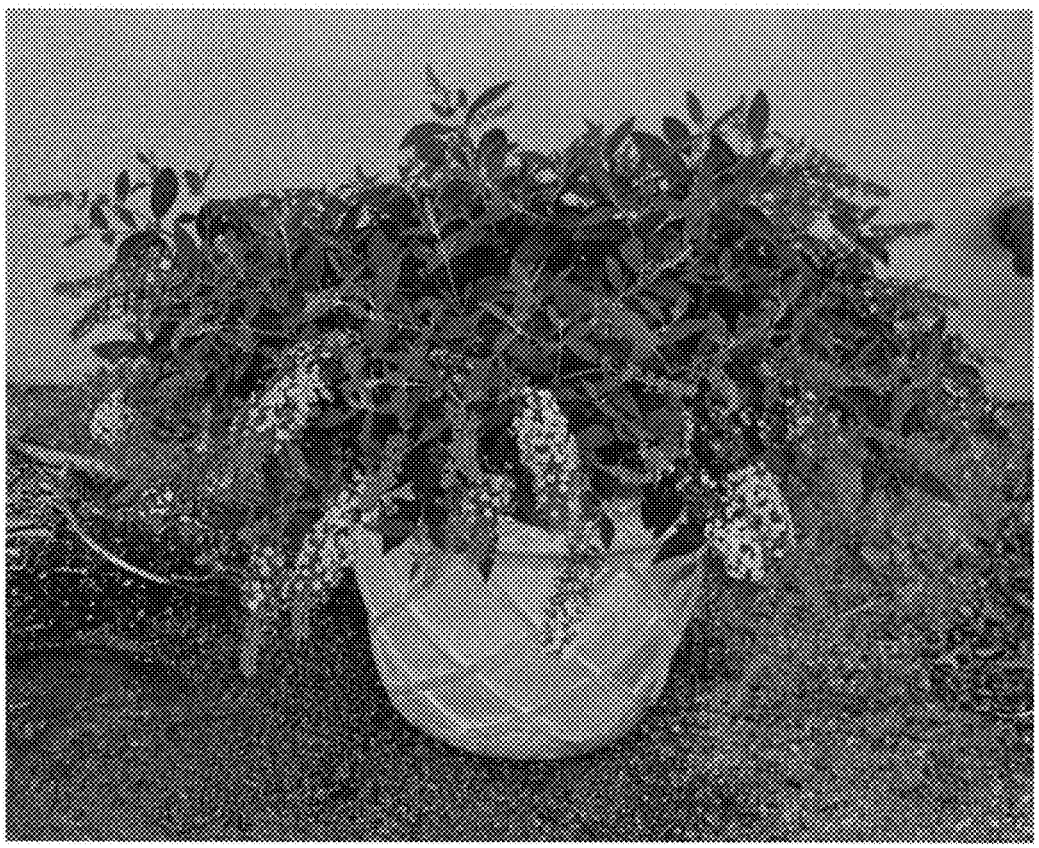
FIG. 1 shows the whole plant, including the habit, foliage and inflorescence.
Figure 2:
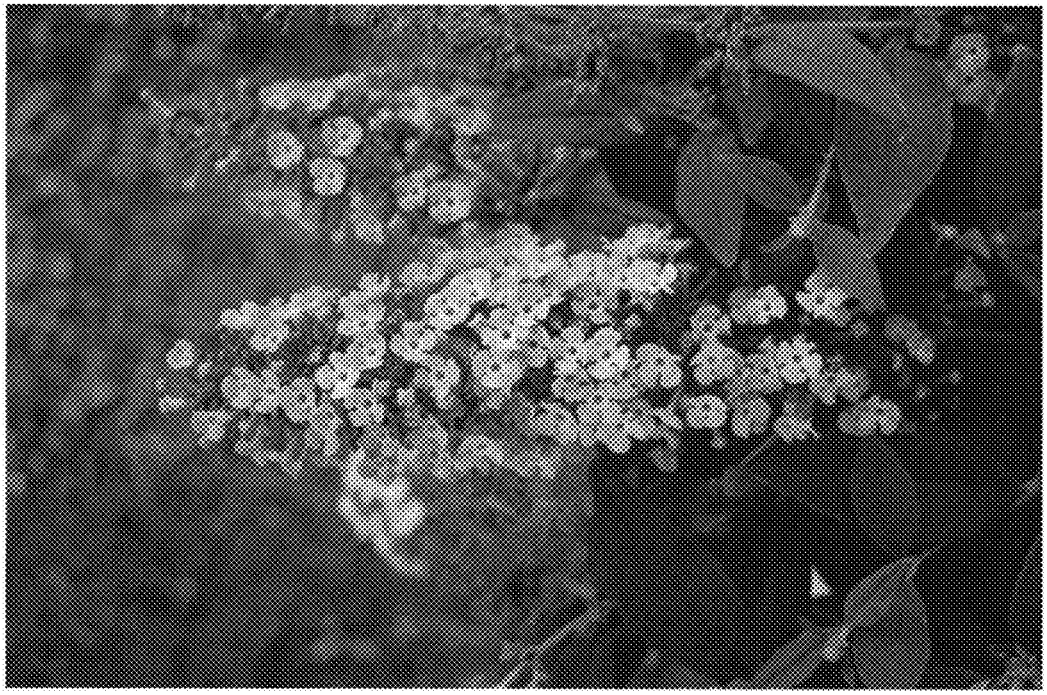
FIG. 2 shows a close-up of the inflorescence and buds.

The following detailed descriptions set forth the distinctive characteristics of 'Hinebud1'. The data which defines these characteristics were collected from asexual reproductions carried out in Winters, Calif. The plant history was taken in August 2011 on one-year old plants grown in a greenhouse and outdoors in Winters, Calif. Color references were taken under natural light and are to The R.H.S. Colour Chart of The Royal Horticultural Society of London (R.H.S.), fifth edition (2007). Texture descriptions were taken using a dissecting microscope.

DESCRIPTION OF THE NEW PLANT

Classification:
- *Family*.—Scrophulariaceae.
- *Botanical name*.—*Buddleia* hybrid.
- *Common name*.—Butterfly bush.
- *Denomination*.—'Hinebud1'.

Plant:
- *Form*.—Shrub.
- *Habit*.—Low growing and spreading.
- *Height* (*measured from the top of the soil*).—38.0 cm.
- *Width* (*horizontal plant diameter*).—65.0 cm.
- *Time to produce a finished plant*.—10 to 12 weeks from a cutting.
- *Outdoor plant performance*.—Excellent and prefers full sun.
- *Time to initiate and develop roots*.—10 to 14 days.

*Root description and habit*.—White, fibrous, dense and branching.

*Propagation type*.—Softwood cuttings.

Lateral branches:

*Quantity per plant*.—Approximately 30.

*Length*.—30.0 cm to 45.0 cm.

*Internode length*.—5.0 cm.

*Diameter* (*from midpoint*).—0.35 cm.

*Color*.—RHS 148B for mature stems.

*Strength*.—Flexible.

*Texture*.—Slightly pubescent.

*Anthocyanin*.—RHS N186B.

Leaves:

*Quantity of leaves per branch*.—8 to 10.

*Arrangement*.—Opposite.

*Length*.—4.5 cm to 9.5 cm, with the average being 8.5 cm.

*Width*.—Up to 3.2 cm.

*Shape*.—Lanceolate.

*Apex*.—Broadly acute.

*Base*.—Acute.

*Margin*.—Serrate.

*Color, immature*.—Upper surface: RHS 139A. Lower surface: RHS 191B.

*Color, mature*.—Upper surface: RHS 137A. Lower surface: RHS 191B.

*Texture*.—Upper surface: Mostly resinous with some oppressed, stellate trichomes. Lower surface: Resinous and densely covered with oppressed overlapping, stellate hairs.

*Venation type*.—Reticulate.

*Venation color*.—Upper surface: RHS 137A. Lower surface: RHS 191A.

*Petiole*.—Color: RHS 146B. Length: 0.5 cm. Diameter: 0.2 cm. Texture: Resinous with many stellate trichomes.

Inflorescence:

*Height*.—15.0 cm to 18.0 cm.

*Width*.—4.5 cm.

*Bud*.—Color: RHS 191C. Shape: Conical. Height: 1.5 cm. Diameter: 0.8 cm.

*Flower*.—Type and habit: Single and salverform shaped flowers arranged in compound terminal panicles; flowers face upright and outward; panicles are roughly conical in shape. Fragrance: Sweetly scented. Flowering season: Early summer to fall. Lastingness of inflorescence on the plant: About one week. Depth: 1.3 cm to 1.5 cm. Diameter: 1.1 cm. Quantity per inflorescence: 180 to 250. Petals: Arrangement and quantity per flower: Four arranged in a single whorl with the petals fused into a narrow tube. Length: 0.4 cm. Width: 0.5 cm. Apex: Rounded and emarginate. Base: Fused. Margin: Crenate. Texture: Upper surface: Very papillate. Lower surface: Papillate with raised veining and scattered stellate trichomes. Color, when opening: Upper surface: RHS N82B. Lower surface: RHS N82B. Color, when open: Upper surface: RHS N82C and fading to RHS 97B. Lower surface: RHS N82C and fading to RHS 97B. Tube: Length: 1.0 cm. Width: 0.2 cm. Color: Inside: RHS 26A. Outside: RHS N77B. Texture: Inside: Papillate with some resinous bodies and upward facing strigose hairs. Outside: Very papillate with scattered glandular bodies. Calyx: Arrangement and quantity: Four sepals arranged in a single whorl and fused towards the base. Shape: Tubular, fitting snugly over the corolla tube. Sepals: Length: 0.4 cm. Width: 0.2 cm. Shape: Ovate. Apex: Broadly acute. Base: Fused with other sepals. Margin: Smooth (entire). Texture: Upper surface: Muricate. Lower surface: Rough and uneven, stellate trichomes with some resinous bodies. Color: Upper surface: RHS 139B. Lower surface: RHS 138A. Peduncle: Length: 2.0 cm to 4.0 cm. Diameter: 0.25 cm. Strength: Flexible. Color: RHS N199B on parts exposed to the sun; RHS 146 on parts not exposed to the sun. Texture: Densely covered with oppressed stellate trichomes. Pedicel: Length: 0.1 cm to 0.3 cm. Diameter: 0.1 cm. Color: RHS 146C. Texture: Covered with oppressed, stellate trichomes.

Reproductive organs:

*Stamens*.—Quantity per flower: 4. Filament: Completely fused to inside of corolla tube; cannot determine length or color. Anther: Length: 0.15 cm. Color: RHS 161B. Pollen amount: Moderate. Pollen color: RHS 155D.

*Pistil*.—Quantity per flower: 1. Length: 0.2 cm. Stigma: Shape: Spatulate with minute cleft at very top. Color: RHS 141B. Style: Length: 0.15 cm. Color: RHS 154C. Ovary: Color: RHS 139C.

Fruit and seed set: Sets seed in presence of other *Buddleia* plants; seed color is RHS 159B and shape is long and narrow, about 0.025 cm by 0.01 cm.

Disease and insect resistance: Susceptible to spider mites.

COMPARISON WITH PARENTAL AND COMMERCIAL VARIETY

'Hinebud1' differs from the un-named female *Buddleia* parent (unpatented) in that 'Hinebud1' is more compact and lower growing.

'Hinebud1' differs from the male *Buddleia* parent 'Podaras #12' (U.S. Plant Pat. No. 22,098) in that 'Hinebud1' is lower growing and has a wider growth habit.

'Hinebud1' differs from the commercial comparison 'Black Knight' (unpatented) in that 'Hinebud1' has a very spreading and low growing habit, while 'Black Knight' has a dense and upright growth habit. Additionally, 'Hinebud1' has a height of less than 2 feet (60.96 cm), while 'Black Knight' has a height of approximately 5 feet to 6 feet (152.4 cm to 183 cm).

I claim:

1. A new and distinct variety of *Buddleia* plant as shown and described herein.

* * * * *